(12) United States Patent
Vavala et al.

(10) Patent No.: US 9,192,721 B2
(45) Date of Patent: Nov. 24, 2015

(54) INFUSION SYSTEM HOUSING MEDICATION SCANNER AND USER INTERFACE DEVICE DISPLAYING DELIVERY DATA

(71) Applicant: CareFusion 303, Inc., San Diego, CA (US)

(72) Inventors: Jill S. Vavala, San Diego, CA (US); Thomas Steinhauer, San Diego, CA (US); Stephen Bollish, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 29 days.

(21) Appl. No.: 13/961,389

(22) Filed: Aug. 7, 2013

(65) Prior Publication Data

US 2015/0041531 A1    Feb. 12, 2015

(51) Int. Cl.
*G06F 17/00*        (2006.01)
*A61M 5/172*        (2006.01)

(52) U.S. Cl.
CPC ....... *A61M 5/172* (2013.01); *A61M 2205/6009* (2013.01); *A61M 2205/6018* (2013.01)

(58) Field of Classification Search
USPC .............................. 235/375, 462.01; 705/2, 3
See application file for complete search history.

(56) References Cited

U.S. PATENT DOCUMENTS

| | | | |
|---|---|---|---|
| 6,519,569 B1* | 2/2003 | White et al. | 705/3 |
| 6,985,870 B2* | 1/2006 | Martucci et al. | 705/3 |
| 2006/0116639 A1* | 6/2006 | Russell | 604/131 |
| 2007/0124177 A1* | 5/2007 | Engleson et al. | 705/3 |
| 2007/0233521 A1* | 10/2007 | Wehba et al. | 705/3 |
| 2013/0197693 A1* | 8/2013 | Kamen et al. | 700/244 |

* cited by examiner

*Primary Examiner* — Tuyen K Vo
(74) *Attorney, Agent, or Firm* — Fred C. Hernandez; Mintz Levin Cohn Ferris Glovsky and Popeo, P.C.

(57) ABSTRACT

The current subject matter describes a delivery of medication to a patient based on a scan of a medication container by a scanner implemented on an infusion system. The medication can include oral medications, injection medications, patches, and/or medication drops. The scanner can scan a machine-readable representation (for example, a barcode) on the medication container to obtain recommended delivery data. A user interface device of the infusion system can display the recommended delivery data on a graphical user interface. Based on the recommended delivery data and based on a patient diagnosis by a clinician, the clinician can determine actual delivery data. Based on the determined actual delivery data, the medication can be delivered to the patient via a non-infusion channel. Related apparatus, systems, techniques and articles are also described.

24 Claims, 15 Drawing Sheets

| DATA TO BE ENTERED BY CLINICIAN TO ACTUATE DISPENSING OF MEDICATION BY MEDICATION CABINET | |
|---|---|
| PROBLEMS TO BE CURED | SPECIFY PROBLEMS — 804 |
| PATIENT CHARACTERISTICS – AGE, HEIGHT, WEIGHT | SPECIFY CHARACTERISTICS — 806 |
| PATIENT SYMPTOMS | SPECIFY SYMPTOMS — 808 |
| CLINICIAN PREFERENCES FOR MEDICATION | SPECIFY PREFERENCES — 810 |
| PATIENT MEDICATION-INTAKE PREFERENCE – PILLS, SHOTS, OR DROPS | SPECIFY INTAKE PREFERENCE — 812 |

FIG. 8

| DATA TO BE ENTERED BY CLINICIAN TO ACTUATE DISPENSING OF MEDICATION BY MEDICATION CABINET | |
|---|---|
| PROBLEMS TO BE CURED | SPECIFY PROBLEMS — 804 |
| PATIENT CHARACTERISTICS – AGE, HEIGHT, WEIGHT | SPECIFY CHARACTERISTICS — 806 |
| PATIENT SYMPTOMS | SPECIFY SYMPTOMS — 808 |
| CLINICIAN PREFERENCES FOR MEDICATION | SPECIFY PREFERENCES — 810 |
| PATIENT MEDICATION-INTAKE PREFERENCE – PILLS, SHOTS, OR DROPS | SPECIFY INTAKE PREFERENCE — 812 |

INFUSION SYSTEM HOUSING MEDICATION SCANNER AND USER INTERFACE DEVICE DISPLAYING DELIVERY DATA

TECHNICAL FIELD

The current subject matter relates to an infusion system that can include a scanner used to scan a medication to obtain recommended delivery data, which can be displayed by a user interface device of the infusion system and based on which the medication can be delivered to a patient via a non-infusion channel.

BACKGROUND

Conventional infusion pumps are known to infuse liquid medications into a body of a patient. These infusion pumps are not designed to deliver non-intravenous medications, such as oral medications, injection medications, patches, and/or medication drops to the patient. To infuse a medication such as oral medications, injection medications, patches, and/or medication drops, a clinician typically delivers the medication to the bedside in a container, such as an intravenous bag. Additionally, the clinician rolls in a conventional computer and a barcode reader. The clinician uses the barcode reader to scan the barcode on the container, wherein the barcode data specifies the name of the medication. The barcode reader sends the barcode data to the computer, which then displays the barcode data. Using this barcode data, the clinician delivers the medication to the patient, and manually notes the details of the delivery on the computer. In this configuration, the clinician is required to use multiple separate devices, such as the infusion pump, the computer, and the barcode reader. These multiple devices occupy a significant amount of physical space. Moreover, it is difficult and inconvenient for the clinician to move and manage these devices.

SUMMARY

The current subject matter describes a delivery of medication to a patient based on a scan of a medication container containing the medication by a scanner included within an infusion system, such as an infusion pump. The medication can include oral medications, injection medications, patches, and/or medication drops. The scanner can scan a machine-readable representation (for example, a barcode) on the medication container to obtain recommended delivery data. A user interface device of the infusion system can display the recommended delivery data on a graphical user interface. The clinician can analyze the recommended delivery data to verify if the recommended delivery data is accurate in view of a diagnosis of the patient by the clinician. Subsequent to the verification and based on the recommended delivery data and the patient diagnosis, the clinician can determine actual delivery data. Based on the determined actual delivery data, the medication can be delivered to the patient via at least one non-infusion channel. The processes described herein can ensure administering of a right dose of a right medication to a right patient at a right time via a right method. Related apparatus, systems, techniques and articles are also described.

In one aspect, an infusion system within a housing can include a scanner and a user interface device attached to the scanner. The scanner can scan a machine-readable representation on a medication container containing a medication to be delivered to a patient via a non-infusion channel. The scanning can generate recommended delivery data associated with the delivery of the medication. The user interface device can execute a graphical user interface displaying the recommended delivery data.

In some variations, one or more of the following can be implemented individually or in any suitable combination. The machine-readable representation can include one or more of: a barcode, a radio frequency identification (RFID) tag, a bokode, and a quick response (QR) code. The medication can include one or more of: at least one oral medication, at least one injection medication, at least one patch, and medication drops. The recommended delivery data can include one or more of: a name of the patient and a patient identifier that can uniquely identify the patient, a name of the medication in the scanned medication container, a recommended quantity of the medication for delivery of the medication, a recommended route of delivering the medication, a time for initiating the delivery of the medication, and an event for initiating the delivery of the medication. A clinician can deliver the medication to the patient via the non-infusion channel in accordance with the recommended delivery data. The non-infusion channel can be at least one of: an oral delivery to a mouth of the patient, a delivery via an injection to a body of the patient, and insertion of medication drops to one of ears, eyes, or nose of the patient. The infusion system can further include a controller and an infusion device connected to the controller. The controller can be connected to the user interface device. The controller can receive data for a delivery of a liquid medication to the patient. The controller can actuate the infusion device to infuse the liquid medication via an infusion channel in accordance with the data for the delivery of the liquid medication. A clinician can deliver the medication within the medication container to the patient via the non-infusion channel while the liquid medication is being infused to the patient via the infusion channel.

In another possible aspect, a system can include a scanner, a user interface device connected to the scanner, and a delivery device. The scanner can scan a machine-readable representation on a medication container containing medication to be delivered to a patient. The scanning can read recommended delivery data for the delivery of the medication. The user interface device can execute a graphical user interface displaying the recommended delivery data. The graphical user interface can receive actual delivery data for the delivery of the medication from a clinician. The delivery device can be actuated based on the actual delivery data to deliver the medication to the patient via at least one non-infusion channel.

In some variations, one or more of the following can be implemented individually or in any suitable combination. The scanner, the user interface device, and the delivery device can be parts of an infusion system. The scanner, the user interface device, and the delivery device can be packaged within a single housing of the infusion system. The system can further include a controller connected to the user interface device and the delivery device. The controller can receive the actual delivery data from the user interface device. The controller can actuate the delivery device based on the actual delivery data. The recommended delivery data can include one or more of: a name of the patient and a patient identifier uniquely identifying the patient, a name of the medication in the scanned medication container, a recommended quantity of the medication for delivery of the medication, a recommended route of delivering the medication, a time for initiating the delivery of the medication, and an event for initiating the delivery of the medication. The actual delivery data can include data characterized by one of a confirmation and an alteration of the recommended delivery data. The system can further include a medication storage device connected to the delivery device. The medical storage device can store the medication contained in the medication container after the scanner scans the machine-readable representation on the medication container. The delivery device can retrieve the medication from the medication storage device before delivering the medication.

In yet another aspect, a user interface device can receive medication selection data. The user interface device can send the medication selection data to a medication storage and delivery system that can include a plurality of medication containers. The medication storage and delivery system can select a medication container based on the medication selection data. A scanner embedded onto the user interface device can scan a machine-readable representation on the medication container to obtain recommended delivery data for the delivery of the medication. The recommended delivery data can be displayed by the user interface device. The user interface device can receive, based on the recommended delivery data, actual delivery data for the delivery of the medication. The medication can be delivered to the patient in accordance with the actual delivery data via at least one non-infusion channel.

In some variations, one or more of the following can be implemented individually or in any suitable combination. The medication selection data can be received from a clinician. The medication selection data can be received at a graphical user interface executed on the user interface device. The medication selection data can be based on a diagnosis of the patient. The diagnosis can include one or more of: problems to be cured, age of the patient, height of the patient, weight of the patient, symptoms of the patient, medication preferences of the clinician, and a medication-intake preference of the patient. The recommended delivery data can be displayed on a graphical user interface executed on the user interface device. The recommended delivery data can include one or more of: a name of the patient and a patient identifier uniquely identifying the patient, a name of the medication in the scanned medication container, a recommended quantity of the medication for delivery of the medication, a recommended route of delivering the medication, a time for initiating the delivery of the medication, and an event for initiating the delivery of the medication. The actual delivery data can be received from a clinician on the graphical user interface executed on the user interface device. The actual delivery data can include data characterized by one of a confirmation and an alteration of the recommended delivery data. The actual delivery data can be sent to a controller. The controller can actuate a delivery device to deliver the medication to the patient based in accordance with the actual delivery data.

In another aspect, a scanner embedded onto a user interface device can scan a machine-readable representation on a medication container to obtain recommended delivery data for the delivery of the medication. The recommended delivery data can be displayed on a graphical user interface of the user interface device. The user interface device can receive, based on the recommended delivery data, actual delivery data for the delivery of the medication. A delivery device actuated by a controller receiving the actual delivery data from the user interface device can deliver the medication to the patient based on the actual delivery data via at least one non-infusion channel.

In some variations, the medication selection data can be received at a remote user interface device. The user interface device can send the medication selection data to a medication storage and delivery system including a plurality of medication containers. The medication storage and delivery system can select the medication container from the plurality of medication containers based on the medication selection data.

Computer program products are also described that comprise non-transitory computer readable media storing instructions, which when executed by at least one data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems.

The subject matter described herein provides many advantages. For example, the implementation of the scanner on the infusion system saves physical space that would have otherwise been occupied by a scanner and a separate infusion system. Further, the implementation of the scanner on the infusion system allows a convenient access of scanned data by the infusion system, thereby preventing a likely human error in manually providing the scanned data to the infusion system. Moreover, the infusion system can enable verification and subsequent administration, orally or by injection, of medication including oral medications, injection medications, patches, and/or medication drops to a patient. Further, in some alternate implementations, the infusion system can enable administration of oral medications, injection medications, patches, and/or medication drops while simultaneously infusing liquid medication (for example, intravenous medication) in a vein of the patient, thereby making the drug/medication delivery procedure efficient.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIG. 8 is a diagram illustrating a first graphical user interface executed by the user interface device;

FIG. 12 is a diagram illustrating a first graphical user interface executed by the remote user interface device;

Like reference symbols in the various drawings indicate like elements.

DETAILED DESCRIPTION

Figure 1:
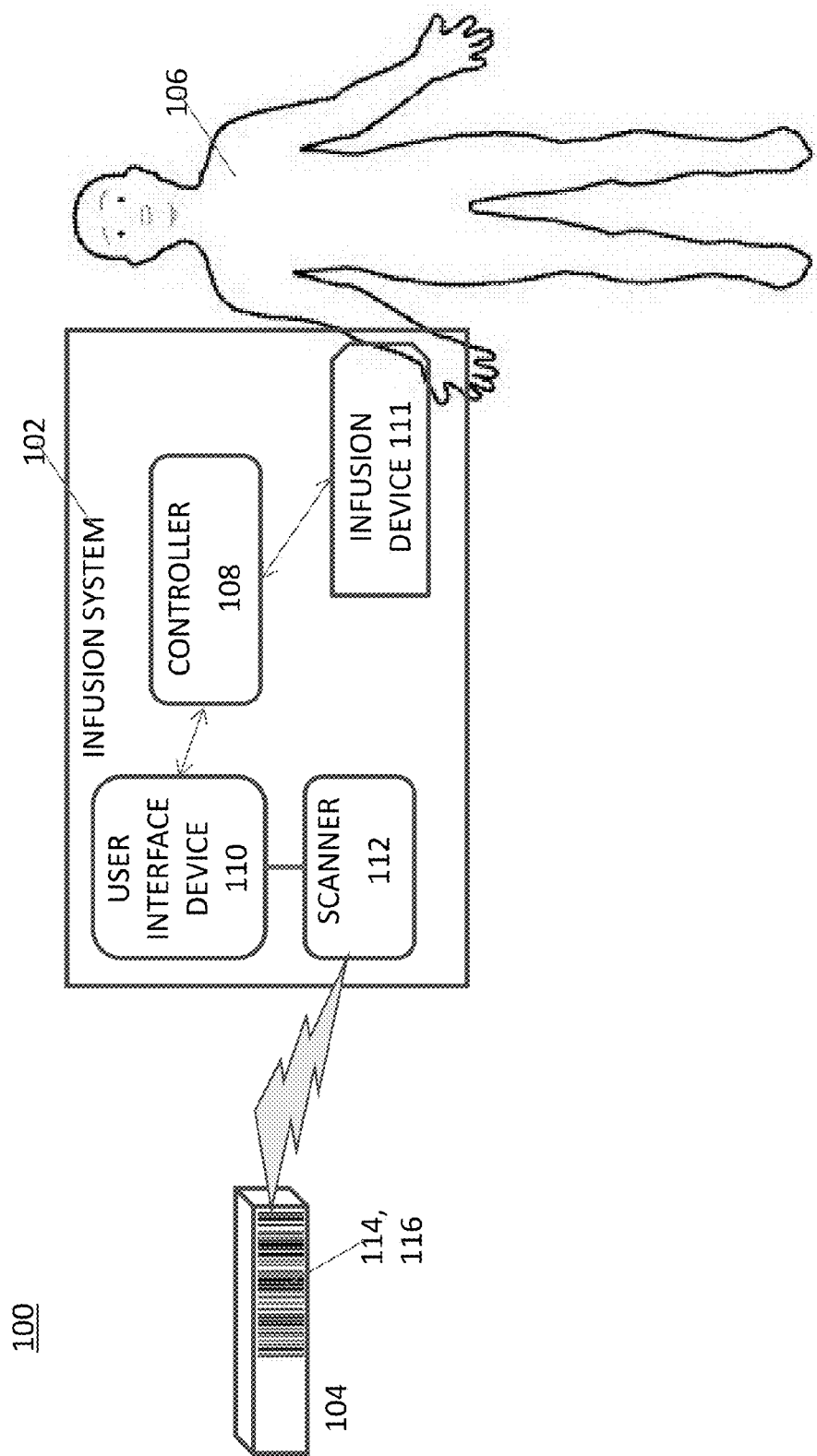
FIG. 1 is a diagram illustrating an infusion system with a scanner that can scan a medication container containing a medication to be delivered to a patient.

FIG. 1 is a diagram 100 illustrating an infusion system 102 with a scanner 112 that can scan a medication container 104 containing a medication to be delivered to a patient 106. In some implementations, the infusion system 102 can be an infusion pump. The medication contained in the medication container 104 can be oral medications, injection medications, patches, and/or medication drops. The infusion system 102 can include a controller 108 that can control a user interface device 110 and an infusion device 111. The clinician can deliver the medication in the medication container 104 to the patient 106 via non-infusion channels. The infusion device 111 can infuse a liquid medication (different from the medication in the medication container 104) to the patient 106 via infusion channels. The user interface device 110 can be connected to the scanner 112. Although the scanner 112 is described as a part of the infusion system 102, in some other implementations, the scanner 112 can be a separate handheld scanner. All components of the infusion system 102 can be packaged within a single compact housing.

The scanner can read a machine-readable representation 114 of data associated with the medication container 104. The machine-readable representation 114 of data can be a barcode 116, and the scanner 112 can be a barcode reader. In other implementations, the machine-readable representation 114 can be one of: a radio frequency identification (RFID) tag, a barcode, a quick response (QR) code, any other machine readable representation, and a combination of two or more of these machine-readable representations. The scanned data can include one or more of: a name of a medication in the container 104, problems expected to be cured by the medication, patient symptoms when the medication is to be delivered, recommended quantity for delivery of the medication, and recommended dosage of the medication. The recommended dosage can include at least one of: one or more initiation times, one or more initiation events, and frequency of delivery of the medication. The scanner 112 then sends the scanned data to the user interface device 110.

The user interface device 110 displays the scanned data in a graphical user interface. Based on the displayed scanned data, a clinician can deliver the medication to the patient 106. The clinician can deliver the medication to the patient 106 via a non-infusion channel. The non-infusion channels can be one of: an oral delivery to a mouth of the patient 106, a delivery via an injection to an arm or a thigh of the patient 106, and insertion of medication drops to one of ears, eyes, or nose of the patient 106. This delivery of medication via non-infusion channels by the clinician can be different from an infusion of a liquid medication by the infusion device 111.

The clinician can be a doctor or a nurse. In some variations, the clinician can be a pharmacist, an assistant or associate in a hospital or laboratory, a psychologist, a psychiatrist, and/or any other authorized individual. In some implementations, the clinician can be the patient 106.

The controller 108 can be one or more of: at least one microcontroller, at least one microprocessor, at least one computer, at least one server, and the like.

The user interface device 110 can be a computer or a tablet computer. The user interface device 110 can be configured to receive an input from a clinician and can be configured to display an output to a clinician. To receive input, the user interface device 110 can be a touch screen device or can be attached with an input device, such as a mouse, a joystick, a keyboard, a voice detection device, or any other input device. To provide output, the user interface device 110 can include a display screen, which can be a cathode ray tube (CRT) monitor, a liquid crystal display (LCD) monitor, a light emitting diode (LED) monitor, or any other display screen.

The infusion device 111 can be a mechanical device that can automatically infuse medications contained within the medication container 104 to the patient 106. These liquid medications can be separate from the medications contained in the medication container 104. The infusion of liquid medications by the infusion device 111 is different from the delivery of the medication in the medication container 104 by the clinician. The controller 108 can control the activations and movements of the infusion device 111. In some implementations, the infusion device 111 can include a plunger and a syringe. The controller 114 can turn a screw that can push on the plunger in accordance with time durations specified by the clinician. Although one infusion device 111 has been described, in other implementations, the infusion pump 102 can include more than one infusion devices. In some implementations, the manual delivery of the medication in the medication container 104 by the clinician and the automatic infusion of the liquid medication by the infusion device 111 can occur simultaneously.

Figure 2:
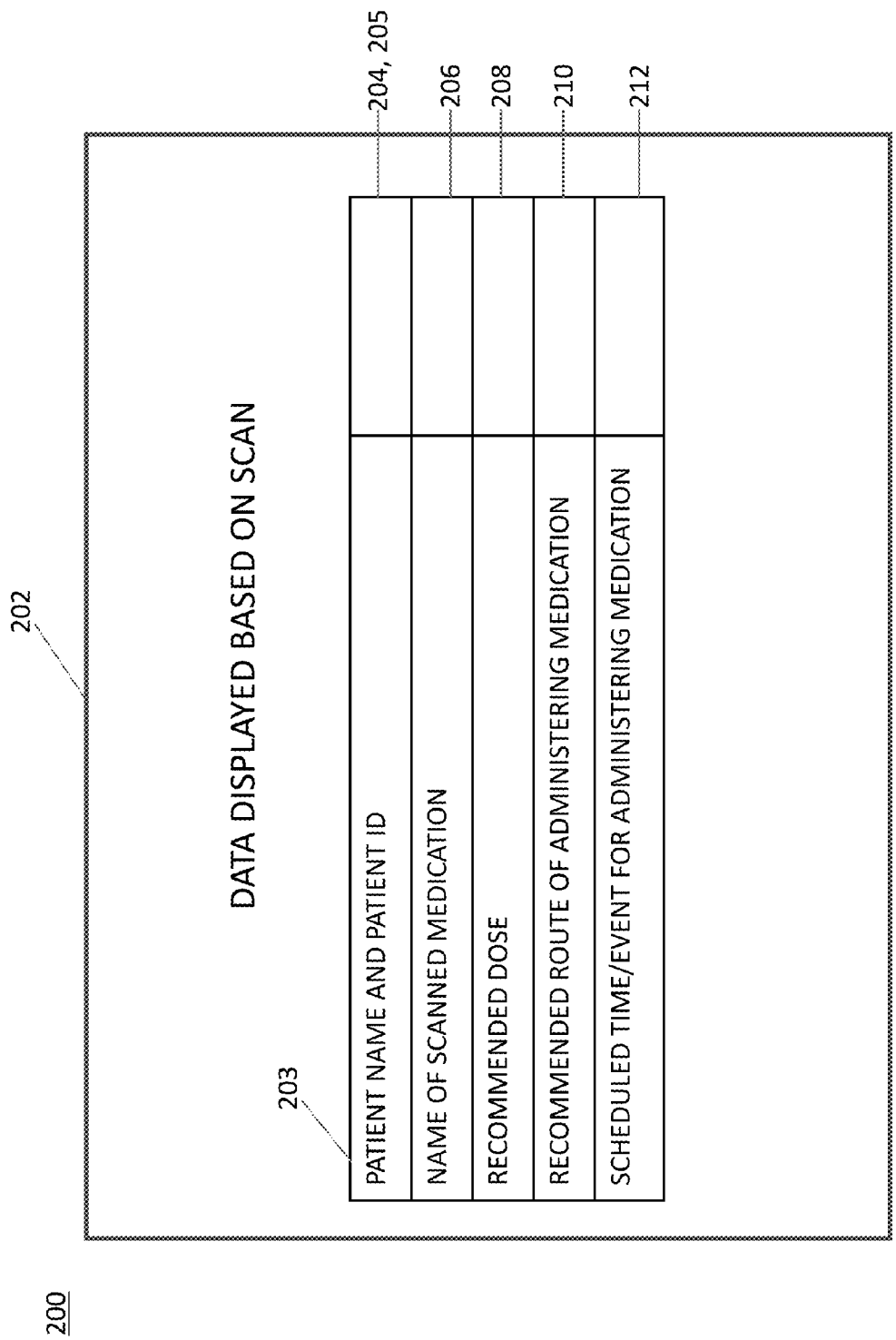
FIG. 2 is a diagram illustrating a graphical user interface displaying a table of scanned data associated with the medication container.

FIG. 2 is a diagram 200 illustrating a graphical user interface 202 displaying a table 203 of scanned data associated with the medication container 104, machine-readable representation 114 of which is scanned by the scanner 112. The user interface device 110 can execute the graphical user interface 202. The displayed data can include one or more of: a name 204 of the patient 106 and a patient identifier 205 uniquely identifying the patient 106, a name 206 of the medication in the scanned medication container 104, recommended dose/quantity 208 of medication for delivery of the medication, a recommended route 210 of delivering the medication, and a scheduled time/event 212 for delivering the medication.

Figure 3:
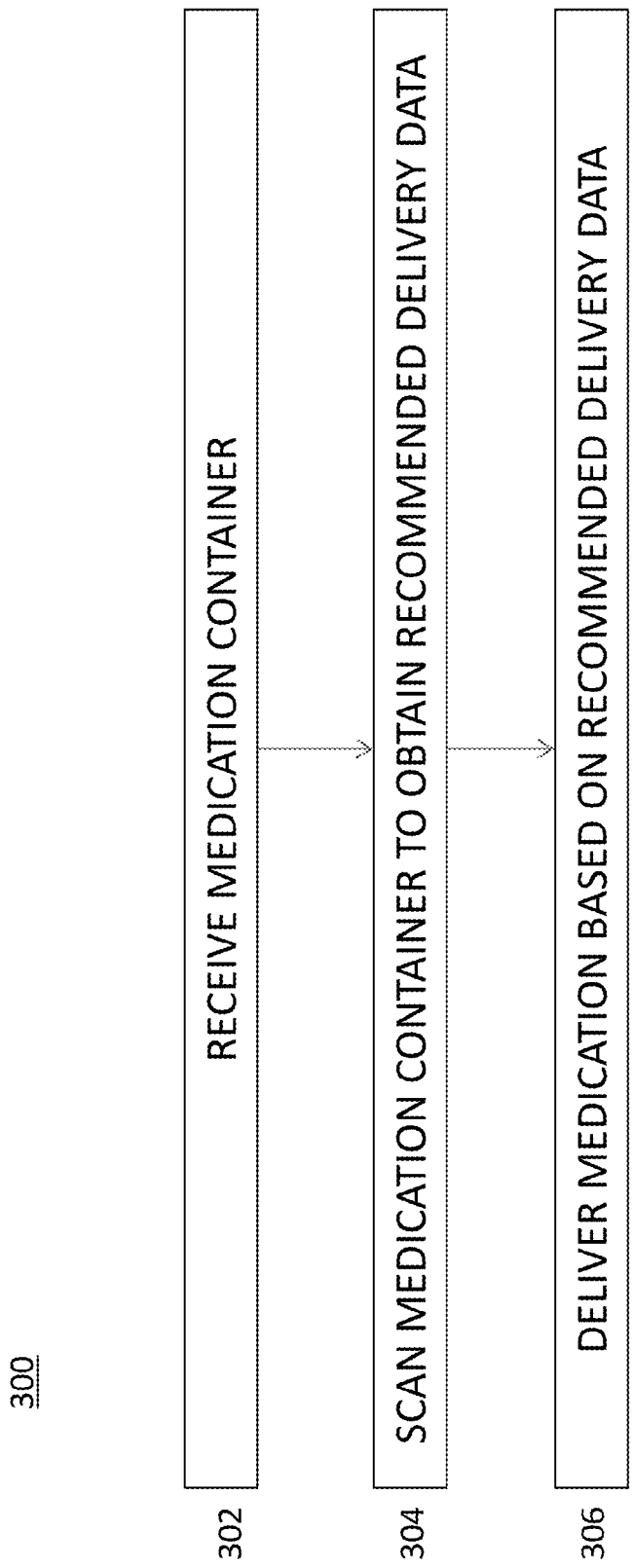
FIG. 3 is a flow diagram illustrating a delivery of a medication based on a scan of a medication container containing the medication.

FIG. 3 is a flow diagram 300 illustrating a delivery of medication based on a scan of a medication container 104 containing the medication. The medication container can be received at 202. More specifically, the clinician can bring the medication container 104 within the range of the scanner 112.

The scanner 112 can scan, at 304, the machine-readable representation 114 on the medication container 104 to obtain automatically recommended delivery data. The automatically recommended delivery data can include one or more of: a name 204 of the patient 106 and a patient identifier 205 uniquely identifying the patient 106, a name 206 of the medication in the scanned medication container 104, recommended dose/quantity 208 of medication for delivery of the medication, a recommended route 210 of delivering the medication, and a scheduled time/event 212 for delivering the medication.

Based on the automatically recommended delivery data, the clinician can deliver, at 306, the medication to the patient 106. The clinician can deliver the medication to the patient 106 orally via the mouth of the patient 106 or by injecting an injection filled with the medication into the body of the patient 106. In some variations, the clinician can deliver the medication to the patient 106 by other ways, such as a topical method, an intramuscular injection, a subcutaneous injection, an inhalational method, a rectal method, and/or any other suitable method.

Figure 4:
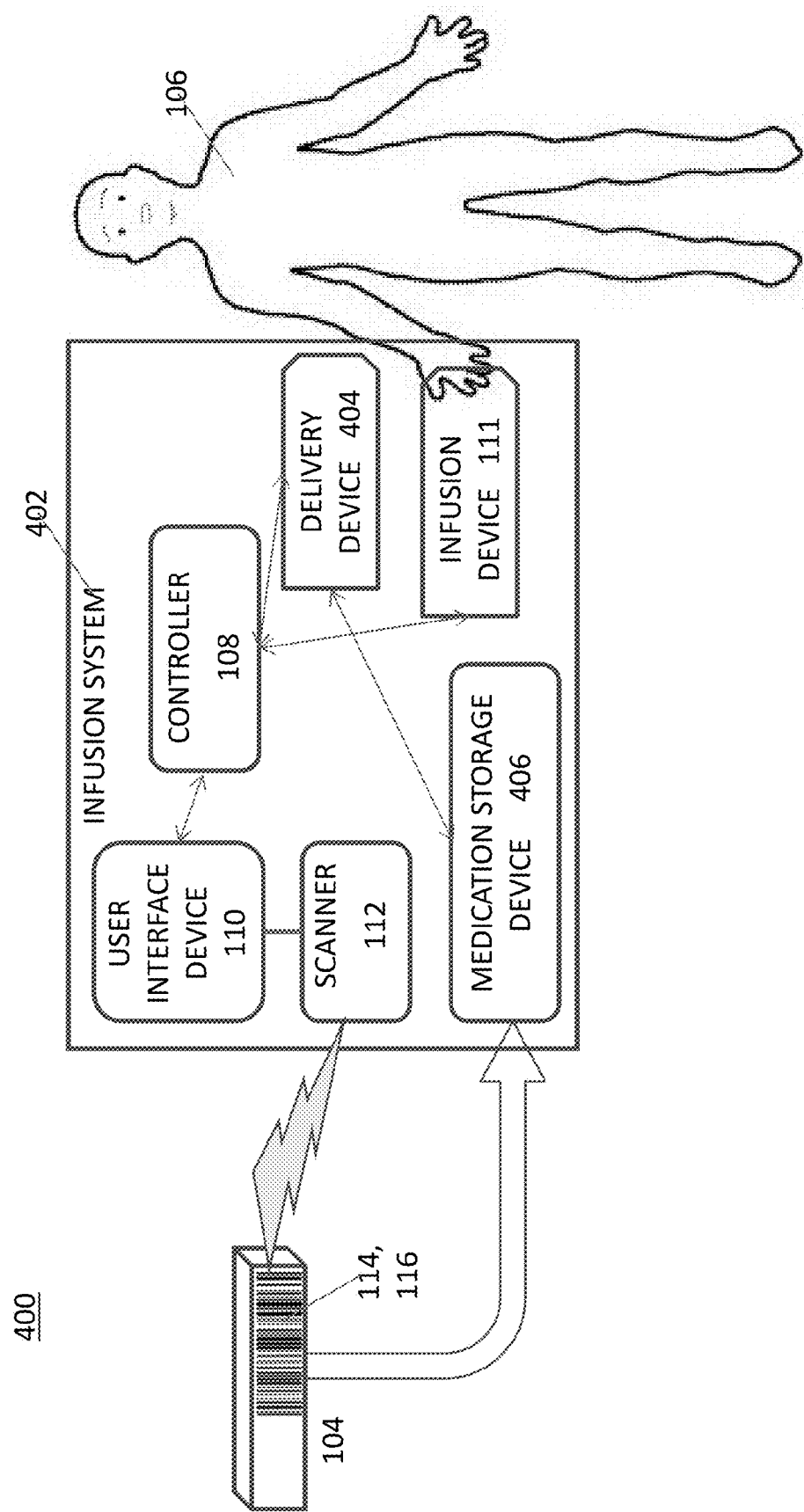
FIG. 4 is a diagram illustrating another infusion system with scanner that can scan a medication container containing a medication to be delivered to a patient.

FIG. 4 is a diagram 400 illustrating another infusion system 402 with a scanner 112 that can scan a medication container 104 containing a medication to be delivered to a patient 106. The medication contained in the medication container 104 can be oral medications, injection medications, patches, medication drops, and/or the like that can be delivered via non-infusion channels. The infusion system 102 can include a controller 108 that can control a user interface device 110, a delivery device 404 to deliver a medication in the medication container 104 via non-infusion channels, and an infusion device 111 to deliver a liquid medication (which is different from the medication in the medication container 104) via infusion channels. The user interface device 110 can be connected to a scanner 112 that can scan the medication container 104. Subsequent to the scan, the medication within the medication container can be stored in a medication storage device 406. The controller 108 can then actuate the delivery device 404 to receive medication from the medication storage device 406 and deliver this stored medication to the patient 106 in accordance with delivery-data specifications confirmed by the clinician on a graphical user interface executed by the user interface device 110.

The delivery-data associated with the delivery of the medication can be stored in a database. The database can be located within the infusion system 402. In other implementations, the database can be located outside the infusion system 102 and can be connected to the infusion 102 system via a communication network, such as a local area network, a wide area network, Internet, a Bluetooth network, an infrared network, or any other network. The database can be a relational database that can include one or more look-up tables, which can include data associated with various patients, health problems, and other data noted herein. A clinician can use a computing device to retrieve, at a later time in future, delivery-data associated with any patient and for any time.

Although a preferred way of delivering the medications can be a manual delivery by the clinician to the patient as described above, in this possible variation, the infusion system 102 can deliver the medication to the patient 106. The delivery device 404 can be a mechanical device that can deliver medications, such as oral medications, injection medications, patches, and/or medication drops to the patient 106. The medication container 104 can contain such medications. The controller 108 can control the activations and movements of the delivery device 404. Although one delivery device 404 has been described, in other implementations, the infusion system 402 can include two or more delivery devices.

Figure 5:
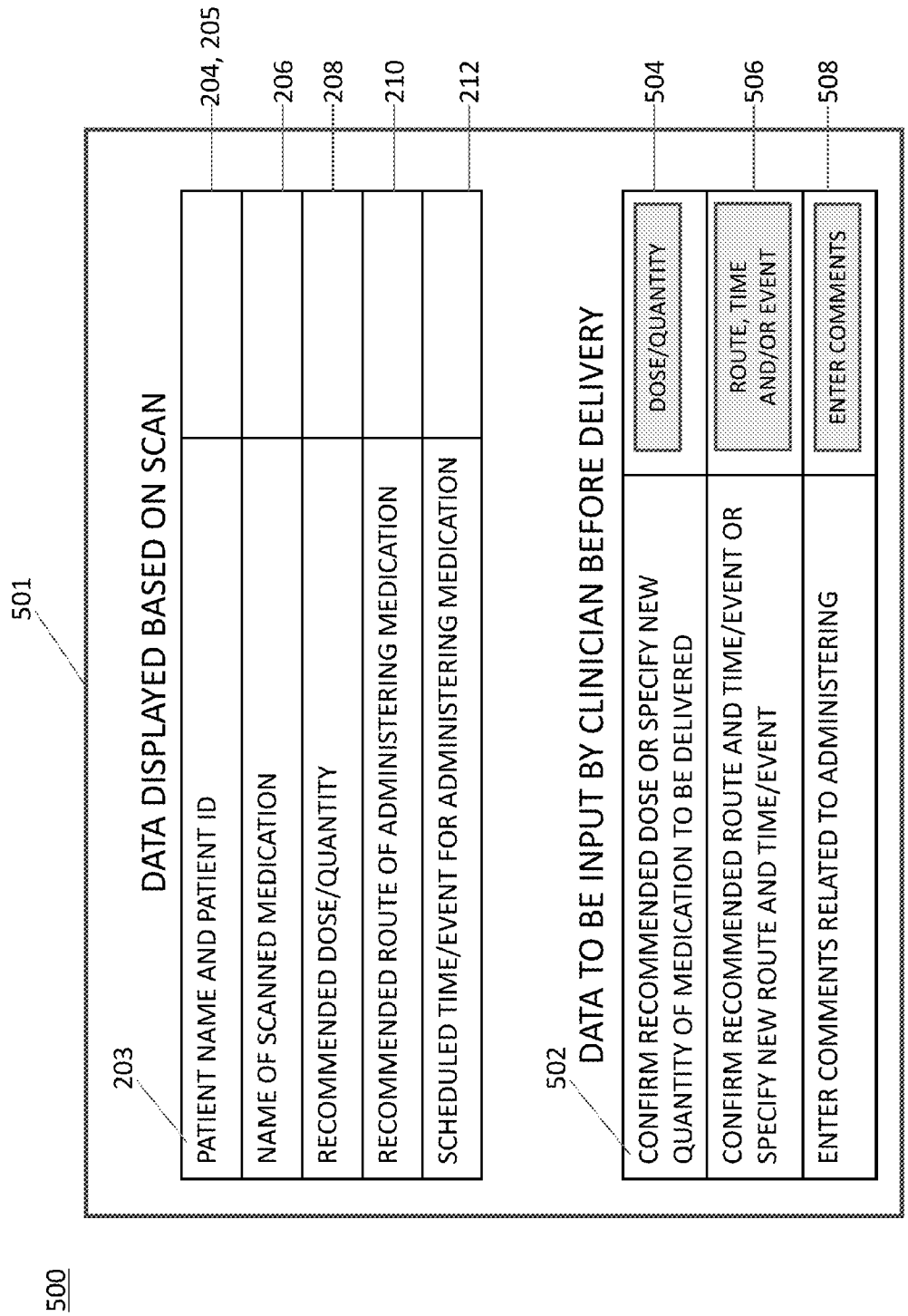
FIG. 5 is a diagram illustrating a graphical user interface displaying tables of data associated with the medication container.

FIG. 5 is a diagram 500 illustrating a graphical user interface 501 displaying tables 203 and 502 of data associated with the medication container 104, machine-readable representation 114 of which is scanned by the scanner 112. The scanner 112 can additionally scan a badge or a band of each of the patient 106 and the clinician. The user interface device 110 can execute the graphical user interface 501. The table 203 can display data based on the scanning. The table 502 can display data specified by the clinician for the delivery of the medication stored in the medication storage device 406.

Table 203 can display data including one or more of: a name 204 of the patient 106 and a patient identifier 205 uniquely identifying the patient 106, a name 206 of the medication in the scanned medication container 104, recommended dose/quantity 208 of medication for delivery of the medication, a recommended route 210 of delivering the medication, and a scheduled time/event 212 for delivering the medication.

Table 502 can require and allow the clinician to provide input for one or more of the following: a confirmation or alteration of dose/quantity 504, a confirmation or alteration of route and time/event 506, and any other comments 508 related to administering/delivery of the medication. In some implementations, when altering values for 504 and 506, the clinician is allowed to select from a set of respective values.

Figure 6:
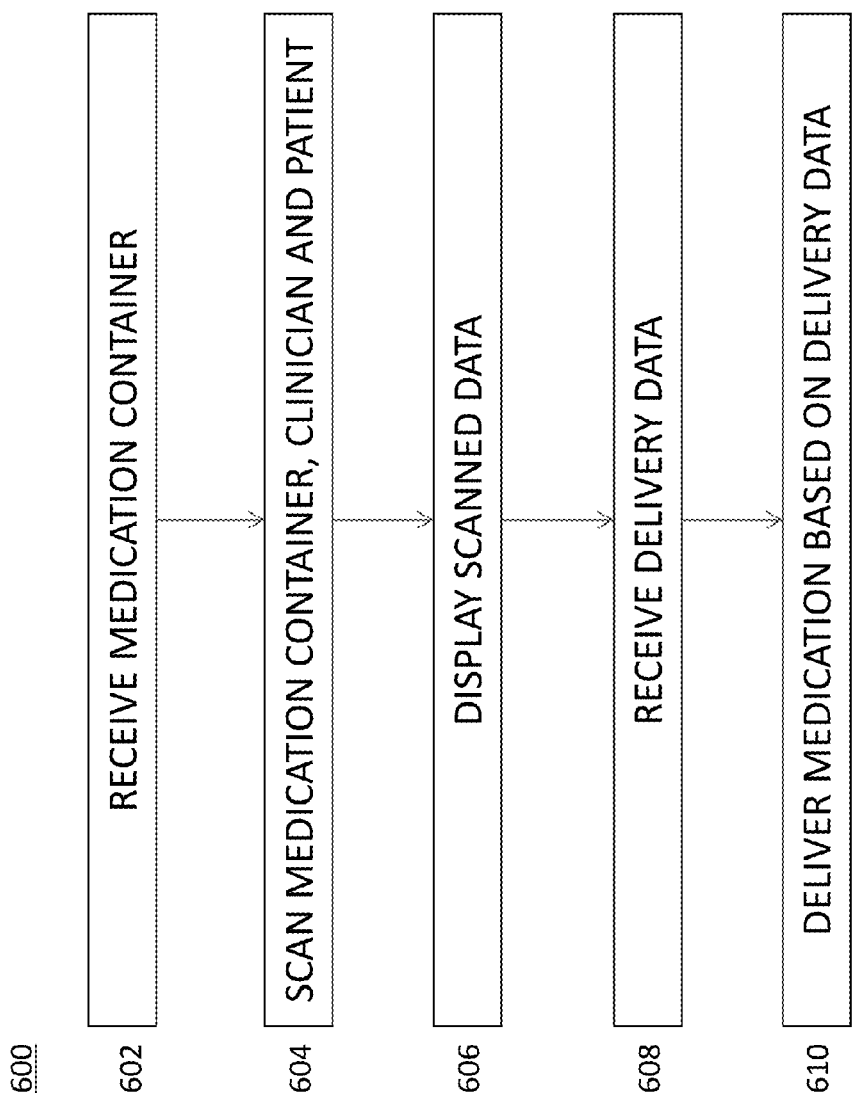
FIG. 6 is a flow diagram illustrating a delivery of a medication based on a scan of the medication container containing the medication.

FIG. 6 is a flow diagram 600 illustrating a delivery of medication based on a scan of a medication container 104 containing the medication. The medication container can be received at 602. More specifically, the medication container 104 can be brought within a detection range of the scanner 112 such that the scanner 112 is able to scan a machine-readable representation 114 on the medication container.

The scanner 112 can scan, at 604, the machine-readable representation 114 on the medication container 104 to obtain scanned data comprising automatically recommended delivery data. The scanner 112 can additionally scan a badge or a band of each of the patient 106 and the clinician to keep a track of the operations associated with the delivery of the medications. The automatically recommended delivery data can include one or more of: a name 204 of the patient 106 and a patient identifier 205 uniquely identifying the patient 106, a name 206 of the medication in the scanned medication container 104, recommended dose/quantity 208 of medication for delivery of the medication, a recommended route 210 of delivering the medication, and a scheduled time/event 212 for delivering the medication.

The graphical user interface 501 displays the scanned data at 606.

The graphical user interface 501 receives, at 608, delivery data from a clinician. The clinician can provide the delivery data based on the displayed scanned data. The controller 108 can actuate the delivery device 404 that can receive medication from the medication storage device 406 in accordance with received delivery data input by the clinician on the graphical user interface 501.

The delivery device 404 can then deliver, at 610, this received medication to the patient 106 either orally via a mouth of the patient 106 or by injecting an injection filled with the medication into the body of the patient 106.

Figure 7:
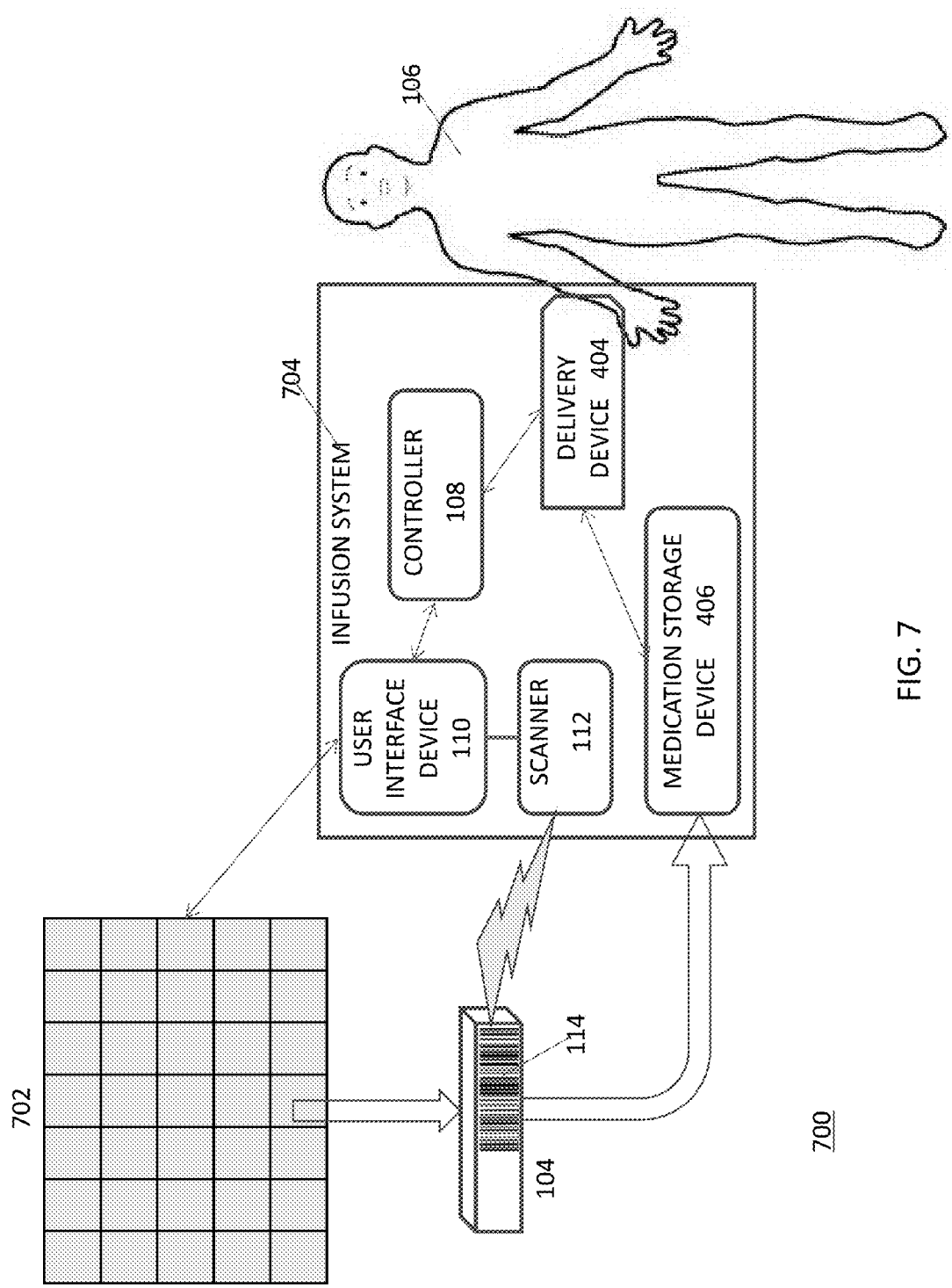
FIG. 7 is a diagram illustrating a delivery of medication in a medication container that is selected from a medication storage and delivery system by using an infusion system.

FIG. 7 is a diagram 700 illustrating a delivery of medication in a medication container 104 that is selected from a medication storage and delivery system 702 by using an infusion system 704. The medical storage and delivery system 702 can be computational medication cabinets in a hospital. In other implementations, the medical storage and delivery system can be a medication ordering system of a pharmacy, a storage and online medication delivery system, and the like.

The medication contained in the medication container 104 can be oral medications, injection medications, patches, medication drops, and/or the like.

The infusion system 704 can include a controller 108 that can control a user interface device 110 and a delivery device 404. A scanner 112 can be attached to the user interface device 110. The scanner 112 can scan the machine-readable representation 114 on the medication container 104. The delivery device 404 can receive medication, which is to be delivered, from a medication storage device 406 that stores the medication within the medication container subsequent to the scan. In some other implementations, the infusion system 702 can further include an infusion device 111 such that the infusion system 704 is same as the infusion system 402.

The user interface device 110 can execute a first graphical user interface that can allow a clinician to input medication selection data including one or more of: problems to be cured, patient characteristics (for example, age, height, weight, and/or other characteristics), patient symptoms, clinician preferences for medication, patient medication-intake preference (for example, oral medications, injection medications, patches, and/or medication drops), and other relevant data. Based on this inputted medication selection data, the medication storage and delivery system 702 can deliver an appropriate medication container 104 containing a desired medication. The scanner 112 can then scan the desired medication. The user interface device 110 can then execute a second graphical user interface that can display the scanned data and request data from the clinician. The clinician can consider the displayed scanned data, and based on this consideration, can specify delivery data on the second graphical user interface for delivery of the medication to the patient 106.

The delivery-data and times associated with the delivery of the medication by the delivery device 404 can be stored in a database. The database can be located within the infusion system 704. In other implementations, the database can be connected to the infusion system via a communication network, such as a local area network, a wide area network, Internet, a Bluetooth network, an infrared network, or any other network. A clinician can use a computing device to retrieve, at a later time in future, delivery-data associated with any patient and for any time.

FIG. 8 is a diagram 800 illustrating a first graphical user interface 802 executed by the user interface device 110. The first graphical user interface 802 can request and receive medication selection data required by the medication storage and delivery system 702 to actuate dispensing of an appropriate medication container 104. The medication selection data can include one or more of: problems 804 to be cured, patient characteristics (for example, age, height, weight, and/or other characteristics) 806, patient symptoms 808, clinician preferences 810 for medication, patient medication-intake preference (for example, oral medications, injection medications, patches, and/or medication drops) 812, and other relevant data. Based on this inputted medication selection data, the medication storage and delivery system 702 can actuate dispensing of an appropriate medication container 104 that can include a desired medication.

Figure 9:
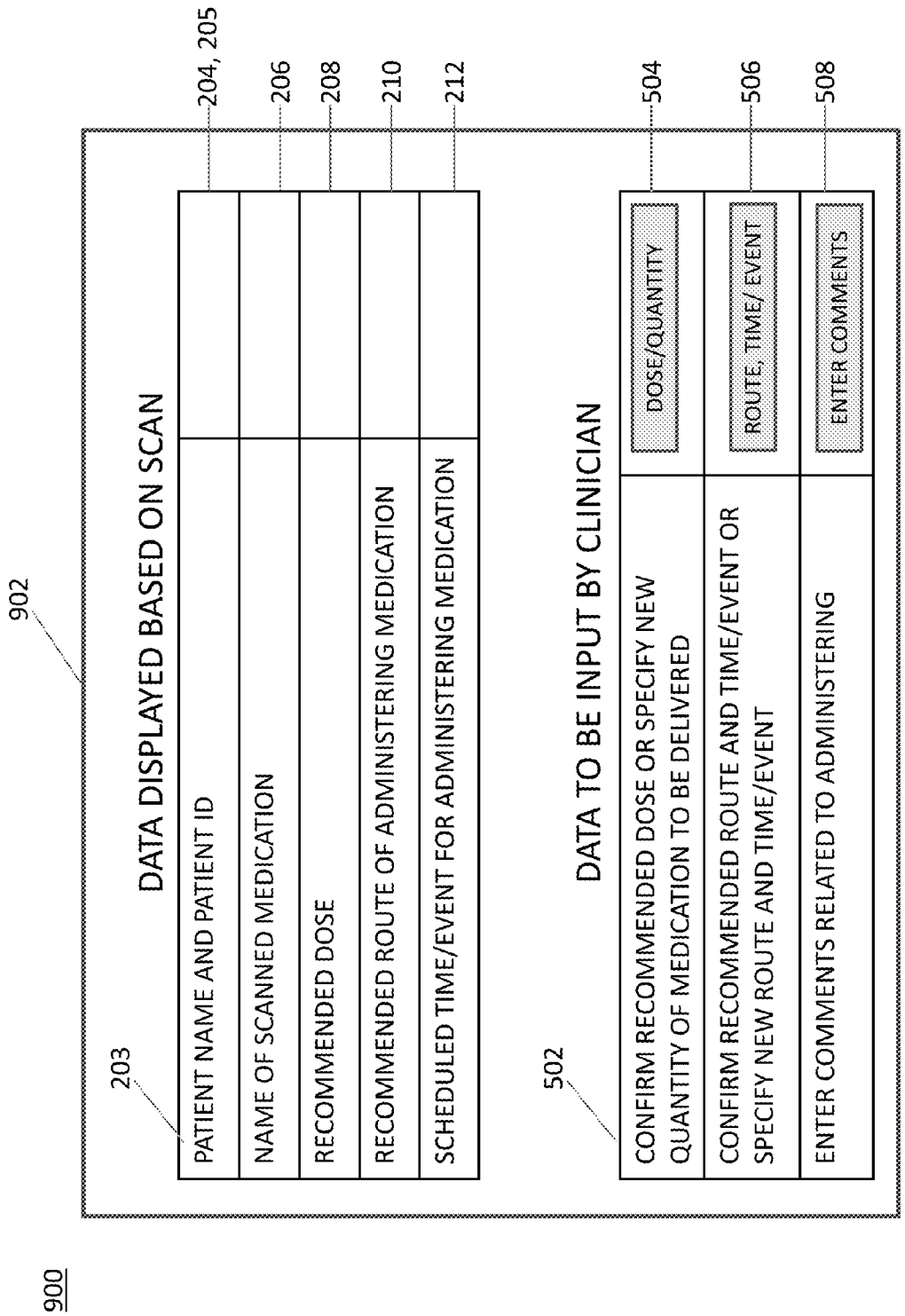
FIG. 9 is a diagram illustrating a second graphical user interface displaying the table including data scanned by the scanner and the table including delivery data requested and obtained from a clinician.

FIG. 9 is a diagram illustrating a second graphical user interface 902 displaying the table 203 including data scanned by the scanner 112 and the table 502 including delivery data requested and obtained from a clinician. The user interface device 110 can execute the second graphical user interface 902.

Table 203 can display data including one or more of: a name 204 of the patient 106 and a patient identifier 205 uniquely identifying the patient 106, a name 206 of the medication in the scanned medication container 104, recommended dose/quantity 208 of medication for delivery of the medication, a recommended route 210 of delivering the medication, and a scheduled time/event 212 for delivering the medication.

Table 502 can require the clinician to provide input for one or more of the following: a confirmation or alteration of dose/quantity 504, a confirmation or alteration of route and time/event 506, and any other comments 508 related to administering/delivery of the medication.

Figure 10:
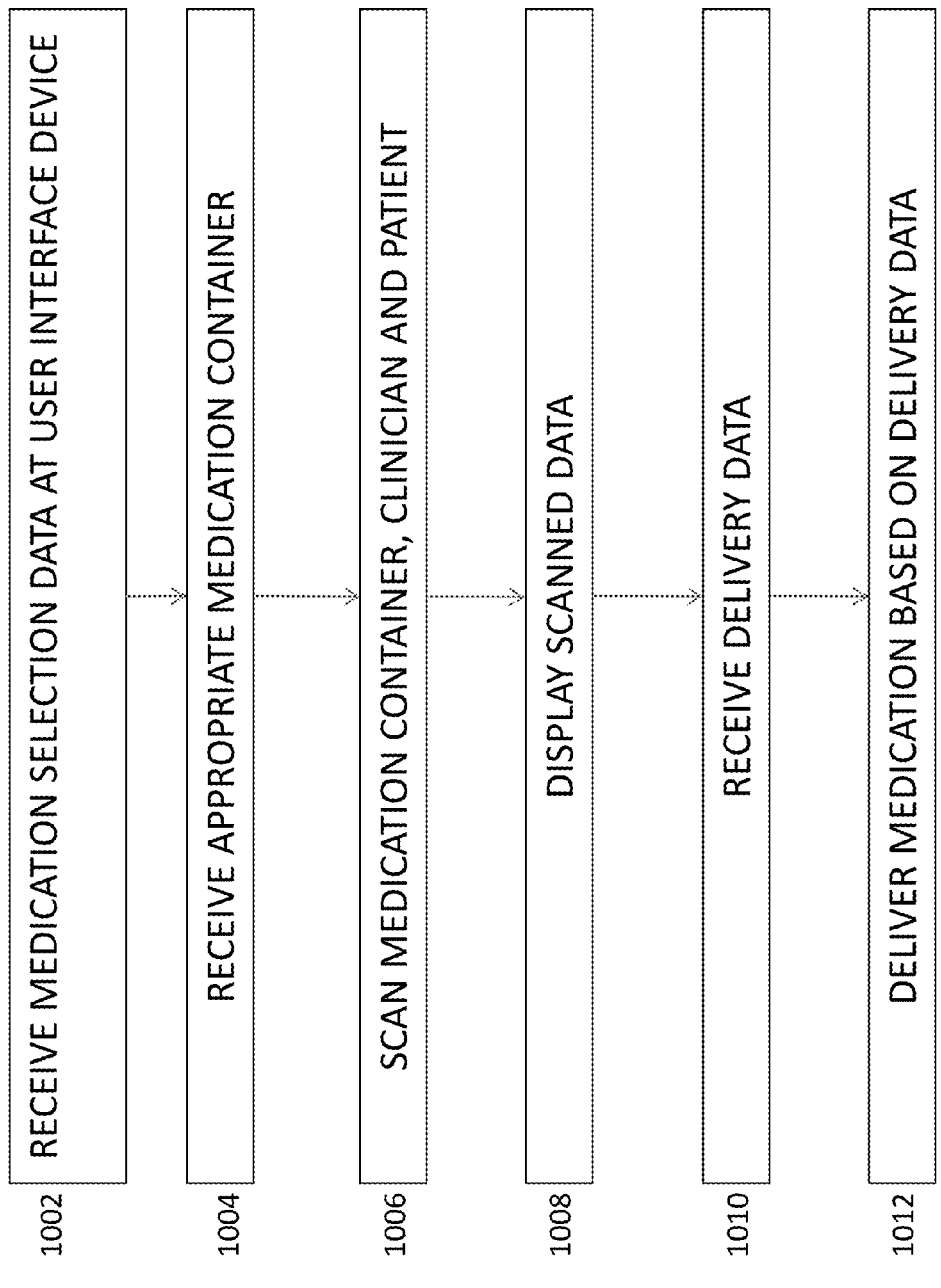
FIG. 10 is a flow diagram illustrating a delivery of medication based on a scan of a medication container containing the medication.

FIG. 10 is a flow diagram 1000 illustrating a delivery of medication based on a scan of a medication container 104 containing the medication. The first graphical user interface 802 implemented on the user interface device 110 can receive, at 1002, medication selection data from a clinician. The user interface device 110 can send this medication selection data to the medication storage and delivery system 702. The medication storage and delivery system 702 can then initiate the delivery of the medication by first matching the medication selection data to stored medication containers. The matched (or closest matched) medication container 102 can be selected.

The infusion system 704 can then receive, at 1004, the matched/selected medication container 104. More specifically, the medication container 104 is brought within the range of the scanner 112.

The scanner can scan a machine-readable representation 114 of the medication container 104 at 1006 to obtain scanned data comprising automatically recommended delivery data. Subsequent to this scan, the medication within the received medication container 104 is stored in the medication storage device 406. The scanner 112 can additionally scan a badge or a band of each of the patient 106 and the clinician to keep a track of the operations associated with the delivery of the medications.

The second graphical user interface 902 can display the scanned data at 1008.

The second graphical user interface 902 can receive, at 1010, delivery data from a clinician. The clinician can input the delivery data based on the displayed scanned data. The controller 108 can actuate the delivery device 404 that can receive medication from the medication storage device 406 in accordance with received delivery data input by the clinician on the second graphical user interface 902. The delivery device 404 can then deliver, at 1012, this received medication to the patient 106 either orally via a mouth of the patient 106 or by injecting an injection filled with the medication into the body of the patient 106.

Figure 11:
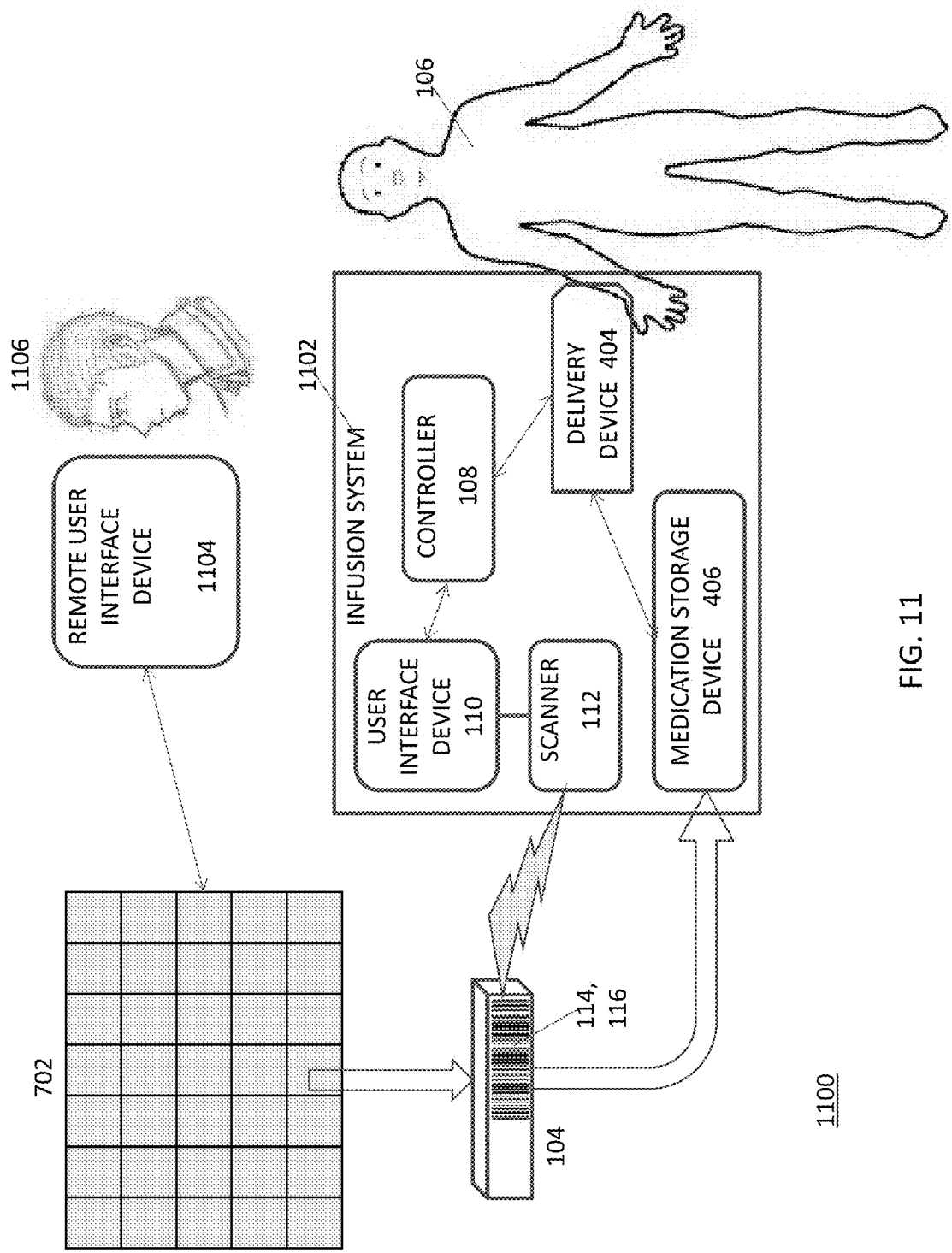
FIG. 11 is a diagram illustrating another infusion system delivering a medication selected based on medication selection data specified on a remote user interface device.

FIG. 11 is a diagram 1100 illustrating another infusion system 1102 delivering a medication selected based on medication selection data specified on a remote user interface device 1104. The medication contained in the medication container 104 can be oral medications, injection medications, patches, medication drops, and/or the like. The infusion system 1102 can include a controller 108 that can control a user interface device 110 and a delivery device 404. A scanner 112 can be attached to the user interface device 110. The scanner 112 can scan the machine-readable representation 114 on the medication container 104. The delivery device 404 can receive medication, which is to be delivered, from a medication storage device 406 that stores the medication within the medication container subsequent to the scan. In some other implementations, the infusion system 702 can further include an infusion device 111 such that the infusion system 704 is same as the infusion system 402.

The remote user interface device 1104 can execute a first graphical user interface that can allow a clinician 1106 to input medication selection data including one or more of: problems 804 to be cured, patient characteristics (for example, age, height, weight, and/or other characteristics) 806, patient symptoms 808, clinician preferences 810 for medication, patient medication-intake preference (for example, oral medications, injection medications, patches, and/or medication drops) 812, and other relevant data. Based on this inputted medication selection data, the medication storage and delivery system 702 can deliver an appropriate medication container 104 that can include a desired medication. The scanner 112 can then scan the desired medication. The user interface device 110 can then execute a second graphical user interface that can display the scanned data and request data from another clinician. In some implementations, the clinician using the user interface device 110 can be same as the clinician 1106 using the remote user interface device. In other implementations, this clinician using the user interface device 110 can be different from the clinician 1106. The clinician using the user interface device 110 can consider the displayed scanned data and specify delivery data on the second graphical user interface for delivery of the medication to the patient 106.

The delivery-data and times associated with the delivery of the medication by the delivery device 404 can be stored in a database. The database can be located within the infusion system 1102. In other implementations, the database can be connected to the infusion system via a communication network, such as a local area network, a wide area network, Internet, a Bluetooth network, an infrared network, or any other network. A clinician can use a computing device to retrieve, at a later time in future, delivery-data associated with any patient and for any time.

FIG. 12 is a diagram 1200 illustrating a first graphical user interface 1202 executed by the remote user interface device 1104. A display of the first graphical user interface 1202 can be same as a display of the first graphical user interface 802. The first graphical user interface 1202 can request and receive medication selection data required by the medication storage and delivery system 702 to actuate dispensing of an appropriate medication container 104. The medication selection data can include one or more of: problems 804 to be cured, patient characteristics (for example, age, height, weight, and/or other characteristics) 806, patient symptoms 808, clinician preferences 810 for medication, patient medication-intake preference (for example, oral medications, injection medications, patches, and/or medication drops) 812, and other relevant data. Based on this inputted medication selection data, the medication storage and delivery system 702 can actuate dispensing of an appropriate medication container 104 that can include a desired medication.

Figure 13:
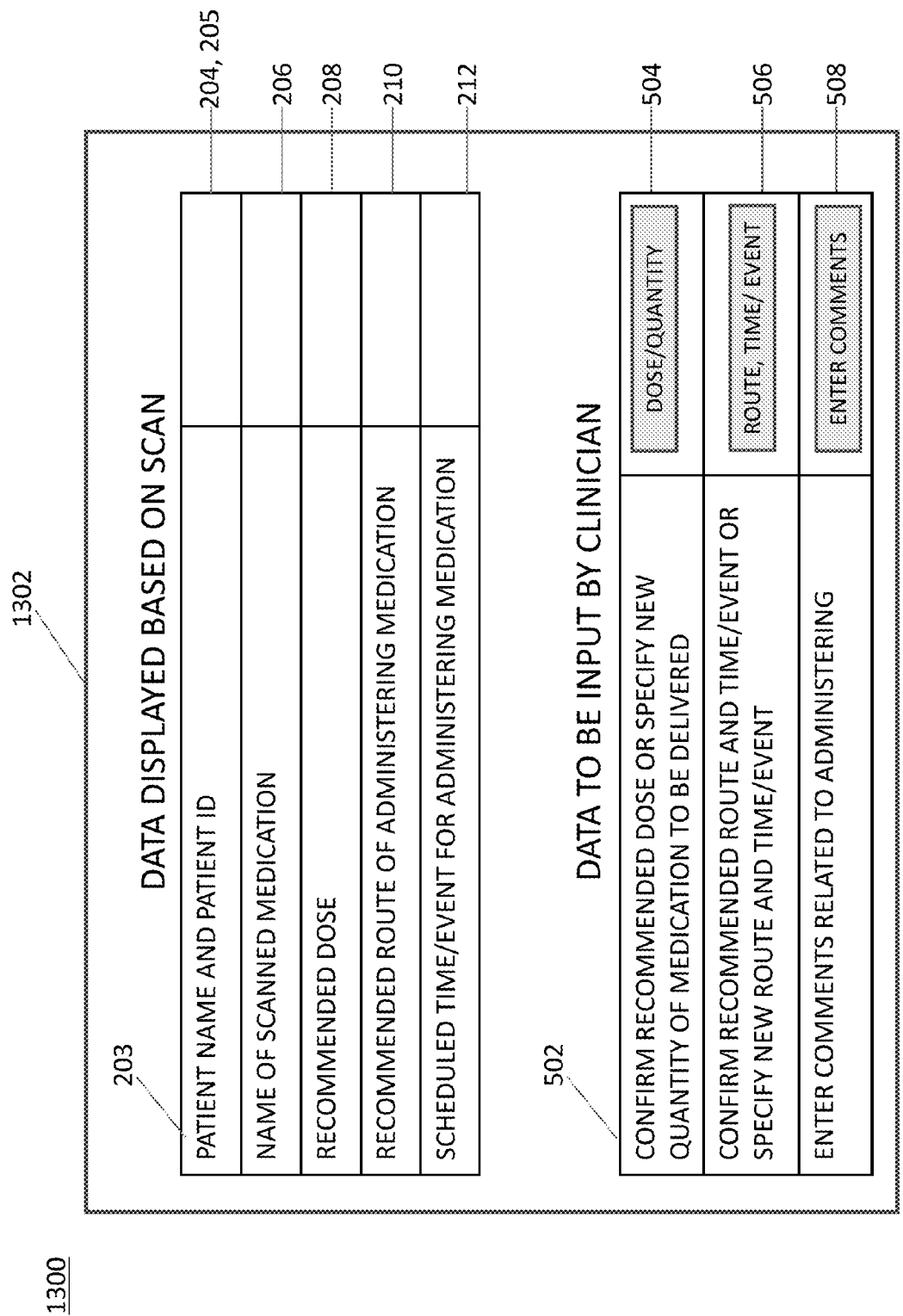
FIG. 13 is a diagram illustrating a second graphical user interface displaying the table including data scanned by the scanner and the table including request of delivery data from a clinician using the user interface device.

FIG. 13 is a diagram illustrating a second graphical user interface 1302 displaying the table 203 including data scanned by the scanner 112 and the table 502 including request of delivery data from a clinician using the user interface device 110. The user interface device 110 can execute the second graphical user interface 1302. A display of the second graphical user interface 1302 can be same as a display of the second graphical user interface 902.

Table 203 can display data including one or more of: a name 204 of the patient 106 and a patient identifier 205 uniquely identifying the patient 106, a name 206 of the medication in the scanned medication container 104, recommended dose/quantity 208 of medication for delivery of the medication, a recommended route 210 of delivering the medication, and a scheduled time/event 212 for delivering the medication.

Table 502 can require the clinician to provide input for one or more of the following: a confirmation or alteration of dose/quantity 504, a confirmation or alteration of route and time/event 506, and any other comments 508 related to administering/delivery of the medication.

Figure 14:
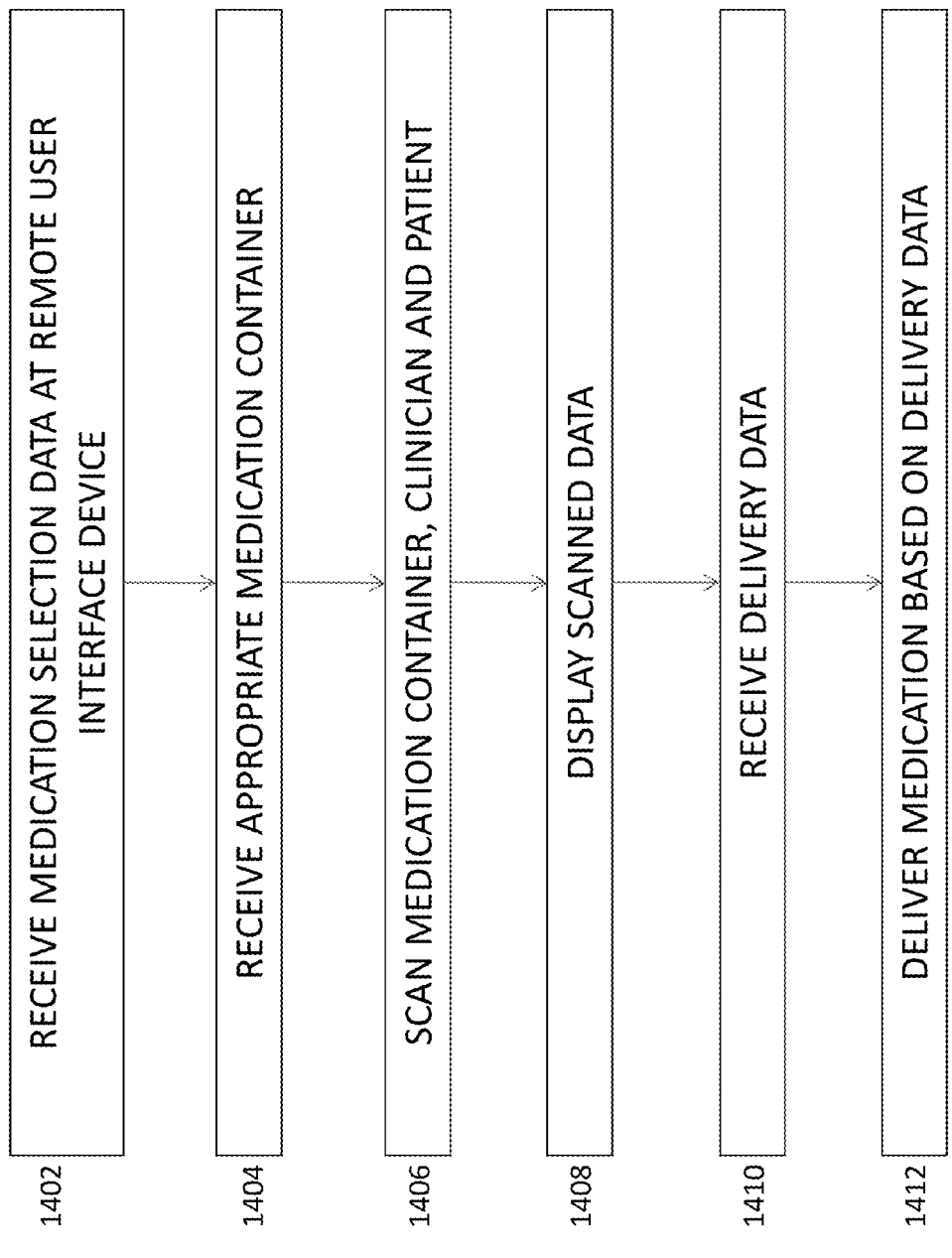
FIG. 14 is a flow diagram illustrating a delivery of medication based on a scan of a medication container containing the medication.

FIG. 14 is a flow diagram 1400 illustrating a delivery of medication based on a scan of a medication container 104 containing the medication. The first graphical user interface 1202 implemented on the remote user interface device 1104 can receive, at 1402, medication selection data from a clinician. The remote user interface device 1104 can send this medication selection data to the medication storage and delivery system 702. The medication storage and delivery system 702 can then initiate the delivery of the medication by first matching the medication selection data to stored medication containers. The matched (or closest matched) medication container 102 can be selected.

The infusion system 704 can then receive, at 1404, the medication container 104. More specifically, the medication container 104 is brought within the range of the scanner 112.

The scanner 112 can scan a machine-readable representation 114 of the medication container 104 at 1406 to obtain scanned data comprising automatically recommended delivery data. Subsequent to this scan, the medication within the received medication container 104 can be stored in the medication storage device 406. The scanner 112 can additionally scan a badge or a band of each of the patient 106 and the clinician to keep a track of the operations associated with the delivery of the medications.

The second graphical user interface 1302 can display the scanned data at 1408.

The second graphical user interface 1302 can receive, at 1410, delivery data from a clinician. The clinician can input the delivery data based on the displayed scanned data. The controller 108 can actuate the delivery device 404 that can receive medication from the medication storage device 406 in accordance with received delivery data input by the clinician on the second graphical user interface 1302. The delivery device 404 can then deliver, at 1012, this received medication to the patient 106 either orally via a mouth of the patient 106 or by injecting an injection filled with the medication into the body of the patient 106.

Figure 15:
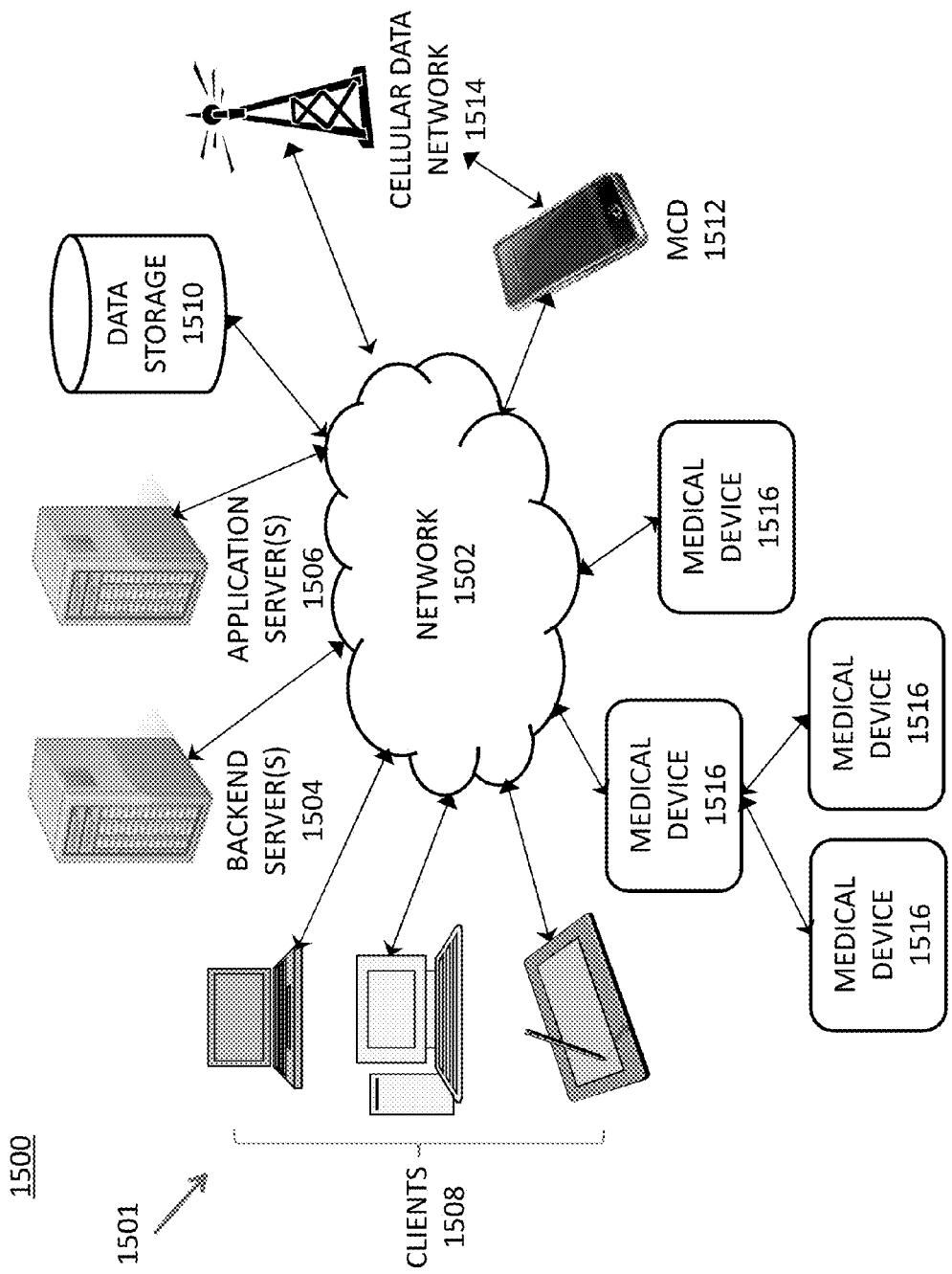
FIG. 15 is a system diagram illustrating a computing landscape that can include the infusion system, the medication storage and delivery system, and the remote user interface device within a healthcare environment.

FIG. 15 is a system diagram 1500 illustrating a computing landscape 1501 that can include the infusion system (102, 402, 704, 1102), the medication storage and delivery system 702, and the remote user interface device 1104 within a healthcare environment, such as a hospital, a clinic, a laboratory, or any other environment. Various devices and systems, both local to the healthcare environment and remote from the healthcare environment, can interact via at least one computing network 1502. This computing network 1502 can provide any form or medium of digital communication connectivity (i.e., wired or wireless) amongst the various devices and systems. Examples of communication networks include a local area network ("LAN"), a wide area network ("WAN"), and the Internet. In some cases, one or more of the various devices and systems can interact directly via peer-to-peer coupling either via a hardwired connection or via a wireless protocol such as, without limitation, short-wavelength radio transmissions (e.g. BLUETOOTH) or the Institute of Electrical and Electronics Engineers' (IEEE) 802.11 standards. In addition, in some variations, one or more of the devices and systems communicate via a cellular data network.

In particular, aspects of the computing landscape 1501 can be implemented in a computing system that includes a back-end component (e.g., as a data server 1504), or that includes a middleware component (e.g., an application server 1506), or that includes a front-end component (e.g., a client computer 1508 having a graphical user interface or a Web browser through which a user can interact with an implementation of the subject matter described herein), or any combination of such back-end, middleware, or front-end components. A client 1508 and servers 1504 and 1506 are generally remote from each other and typically interact through the communications network 1502. The relationship of the clients 1508 and servers 1504, 1506 arises by virtue of computer programs running on the respective computers and having a client-server relationship to each other. Clients 1508 can be any of a variety of computing platforms that include local applications for providing various functionalities within the healthcare environment. Example clients 1508 include, but are not limited to, desktop computers, laptop computers, tablets, and other computers with touch-screen interfaces. The local applications can be self-contained in that they do not require network connectivity and/or they can interact with one or more of the servers 1504, 1506 (e.g., a web browser).

A variety of applications can be executed on the various devices and systems within the computing landscape such as electronic health record applications, medical device monitoring, operation, and maintenance applications, scheduling applications, billing applications and the like.

The network 1502 can be coupled to one or more data storage systems 1510. The data storage systems 1510 can include databases providing physical data storage within the healthcare environment or within a dedicated facility. In addition, or in the alternative, the data storage systems 1510 can include cloud-based systems providing remote storage of data in, for example, a multi-tenant computing environment. The data storage systems 1510 can also comprise non-transitory computer readable media.

Mobile communications devices 1512 can also form part of the computing landscape 1501. The mobile communication devices 1512 can communicate directly via the network 1502 and/or they can communicate with the network 1502 via an intermediate network such as a cellular data network 1514. The mobile communication devices 1512 can use various types of communication protocols, such as messaging protocols, examples of which can include short messaging service (SMS) and multimedia messaging service (MMS).

Various types of medical devices 1516 can be used as part of the computing landscape 1501. The medical devices 1516 can include one or more of the infusion system (102, 402, 704, 1102), the medication storage and delivery system 702, and the remote user interface device 1104. These medical devices 1516 can include, unless otherwise specified, any type of device or system with a communications interface that characterizes one or more physiological measurements of a patient and/or that characterize treatment of a patient. In some cases, the medical devices 1516 communicate via peer to peer wired or wireless communications with another medical device 1516 (as opposed to communicating with the network 1502). For example, the medical device 1516 can comprise a bedside vital signs monitor that is connected to other medical devices 1516, namely a wireless pulse oximeter and to a wired blood pressure monitor. One or more operational parameters of the medical devices 1516 can be locally controlled by a clinician, controlled via a clinician via the network 1502, and/or they can be controlled by one or more of a server 1504 and/or 1506, a client 1508, a mobile communication device 1512, and/or another medical device 1516.

The computing landscape 1501 can provide various types of functionality as can be required within a healthcare environment such as a hospital. For example, a pharmacy can initiate a prescription via one of the client computers 1508. This prescription can be stored in the data storage 1510 and/or pushed out to other clients 1508, a mobile communication device 1512, and/or one or more of the medical devices 1516. In addition, the medical devices 1516 can provide data characterizing one or more physiological measurements of a patient and/or treatment of a patient (e.g., medical device 1516 can be an infusion management system, etc.). The data generated by the medical devices 1516 can be communicated to other medical devices 1516, the servers 1504 and 1506, the clients 1508, the mobile communication devices 1512, and/or stored in the data storage systems 1510.

Various implementations of the subject matter described herein can be realized/implemented in digital electronic circuitry, integrated circuitry, specially designed application specific integrated circuits (ASICs), computer hardware, firmware, software, and/or combinations thereof. These various implementations can be implemented in one or more computer programs. These computer programs can be executable and/or interpreted on a programmable system. The programmable system can include at least one programmable processor, which can be have a special purpose or a general purpose. The at least one programmable processor can be coupled to a storage system, at least one input device, and at least one output device. The at least one programmable processor can receive data and instructions from, and can transmit data and instructions to, the storage system, the at least one input device, and the at least one output device.

These computer programs (also known as programs, software, software applications or code) can include machine instructions for a programmable processor, and can be implemented in a high-level procedural and/or object-oriented programming language, and/or in assembly/machine language. As can be used herein, the term "machine-readable medium" can refer to any computer program product, apparatus and/or device (for example, magnetic discs, optical disks, memory, programmable logic devices (PLDs)) used to provide machine instructions and/or data to a programmable processor, including a machine-readable medium that can receive machine instructions as a machine-readable signal. The term "machine-readable signal" can refer to any signal used to provide machine instructions and/or data to a programmable processor.

To provide for interaction with a user, the subject matter described herein can be implemented on a computer that can display data to one or more users on a display device, such as a cathode ray tube (CRT) device, a liquid crystal display (LCD) monitor, a light emitting diode (LED) monitor, or any other display device. The computer can receive data from the one or more users via a keyboard, a mouse, a trackball, a joystick, or any other input device. To provide for interaction with the user, other devices can also be provided, such as devices operating based on user feedback, which can include sensory feedback, such as visual feedback, auditory feedback, tactile feedback, and any other feedback. The input from the user can be received in any form, such as acoustic input, speech input, tactile input, or any other input.

The subject matter described herein can be implemented in a computing system that can include at least one of a back-end component, a middleware component, a front-end component, and one or more combinations thereof. The back-end component can be a data server. The middleware component can be an application server. The front-end component can be a client computer having a graphical user interface or a web browser, through which a user can interact with an implementation of the subject matter described herein. The components of the system can be interconnected by any form or medium of digital data communication, such as a communication network. Examples of communication networks can include a local area network, a wide area network, internet, intranet, Bluetooth network, infrared network, or other networks.

The computing system can include clients and servers. A client and server can be generally remote from each other and can interact through a communication network. The relationship of client and server can arise by virtue of computer programs running on the respective computers and having a client-server relationship with each other.

Although a few variations have been described in detail above, other modifications can be possible. For example, the logic flows depicted in the accompanying figures and described herein do not require the particular order shown, or sequential order, to achieve desirable results. Other embodiments may be within the scope of the following claims.

What is claimed is:

1. An infusion system within a housing, the infusion system comprising:
   a scanner to scan a machine-readable representation on a medication container containing a medication to be delivered to a patient via a non-infusion channel, the scanning generating recommended delivery data associated with the delivery of the medication while simultaneously infusing a liquid medication to the patient via an infusion channel; and
   a user interface device attached to the scanner, the user interface device executing a graphical user interface displaying the recommended delivery data.

2. The infusion system of claim 1, wherein the machine-readable representation comprises one or more of: a barcode, a radio frequency identification (RFID) tag, a bokode, and a quick response (QR) code.

3. The infusion system of claim 1, wherein the medication comprises one or more of: at least one oral medication, at least one injection medication, at least one patch, and medication drops.

4. The infusion system of claim 1, wherein the recommended delivery data includes one or more of: a name of the patient and a patient identifier uniquely identifying the patient, a name of the medication in the scanned medication container, a recommended quantity of the medication for delivery of the medication, a recommended route of delivering the medication, a time for initiating the delivery of the medication, and an event for initiating the delivery of the medication.

5. The infusion system of claim 1, wherein a clinician delivers the medication to the patient via the non-infusion channel in accordance with the recommended delivery data, the non-infusion channel being at least one of: an oral delivery to a mouth of the patient, a delivery via an injection to a body of the patient, and insertion of medication drops to one of ears, eyes, or nose of the patient.

6. The infusion system of claim 1, further comprising:
   a controller connected to the user interface device, the controller receiving data for a delivery of a liquid medication to the patient; and
   an infusion device connected to the controller, the controller actuating the infusion device to infuse the liquid medication via an infusion channel in accordance with the data for the delivery of the liquid medication.

7. The infusion pump of claim 6, wherein a clinician delivers the medication within the medication container to the patient via the non-infusion channel while the liquid medication is being infused to the patient via the infusion channel.

8. The system of claim 1, wherein the user interface device: receives user-generated input comprising medication selection data, and sends the medication selection data over a network to a medication storage and delivery system comprising a plurality of medication containers, the medication storage and delivery system selecting a medication container based on the medication selection data.

9. A system comprising:
   a scanner to scan a machine-readable representation on a medication container containing medication to be delivered to a patient, the scanning reading recommended delivery data for the delivery of the medication;
   a user interface device connected to the scanner, the user interface device executing a graphical user interface displaying the recommended delivery data, the graphical user interface receiving actual delivery data for the delivery of the medication from a clinician; and
   a delivery device being actuated based on the actual delivery data to deliver the medication to the patient via at least one non-infusion channel, the delivery device infusing a liquid medication to the patient when the medication is being delivered via the at least one non-infusion channel;
   wherein:
      the scanner, the user interface device, and the delivery device are parts of an infusion system; and
      the scanner, the user interface device, and the delivery device are packaged within a single housing of the infusion system.

10. The system of claim 9, further comprising:
    a controller connected to the user interface device and the delivery device, the controller receiving the actual delivery data from the user interface device, the controller actuating the delivery device based on the actual delivery data.

11. The system of claim 9, wherein the recommended delivery data comprises one or more of: a name of the patient and a patient identifier uniquely identifying the patient, a name of the medication in the scanned medication container, a recommended quantity of the medication for delivery of the medication, a recommended route of delivering the medication, a time for initiating the delivery of the medication, and an event for initiating the delivery of the medication.

12. The system of claim 9, wherein the actual delivery data comprises data characterized by one of a confirmation and an alteration of the recommended delivery data.

13. The system of claim 9, further comprising:
    a medication storage device connected to the delivery device, the medical storage device storing the medication contained in the medication container after the scanner scans the machine-readable representation on the medication container.

14. The system of claim 13, wherein the delivery device retrieves the medication from the medication storage device before delivering the medication.

15. A method comprising:
    receiving medication selection data at a user interface device forming part of an infusion system, the user interface device sending the medication selection data over a network to a medication storage and delivery system comprising a plurality of medication containers, the medication storage and delivery system selecting a medication container based on the medication selection data;
    scanning, by a scanner embedded onto the user interface device, a machine-readable representation on the medication container to obtain recommended delivery data for the delivery of the medication, the recommended delivery data being displayed by the user interface device;
receiving, at the user interface device and based on the recommended delivery data, actual delivery data for the delivery of the medication; and
delivering the medication to the patient in accordance with the actual delivery data via at least one non-infusion channel, a liquid medication being infused to the patient during the delivery via an infusion channel, the liquid medication being different from the medication to the patient in accordance with the actual delivery data via at least one non-infusion channel.

16. The method of claim 15, wherein the medication selection data is received from a clinician, the medication selection data being received at a graphical user interface executed on the user interface device.

17. The method of claim 15, wherein:
the medication selection data is based on a diagnosis of the patient; and
the diagnosis comprises one or more of: problems to be cured, age of the patient, height of the patient, weight of the patient, symptoms of the patient, medication preferences of the clinician, and a medication-intake preference of the patient.

18. The method of claim 15, wherein the recommended delivery data is displayed on a graphical user interface executed on the user interface device.

19. The method of claim 18, wherein the recommended delivery data comprises one or more of: a name of the patient and a patient identifier uniquely identifying the patient, a name of the medication in the scanned medication container, a recommended quantity of the medication for delivery of the medication, a recommended route of delivering the medication, a time for initiating the delivery of the medication, and an event for initiating the delivery of the medication.

20. The method of claim 18, wherein the actual delivery data is received from a clinician on the graphical user interface executed on the user interface device.

21. The method of claim 20, wherein the actual delivery data comprises data characterized by one of a confirmation and an alteration of the recommended delivery data.

22. The method of claim 15, wherein the actual delivery data is sent to a controller, the controller actuating a delivery device to deliver the medication to the patient based in accordance with the actual delivery data.

23. A non-transitory computer program product storing instructions that, when executed by at least one programmable processor, cause the at least one programmable processor to perform operations comprising:
receiving medication selection data at a first user interface device, the user interface device sending the medication selection data to a medication storage and delivery system comprising a plurality of medication containers, the medication storage and delivery system selecting the medication container from the plurality of medication containers based on the medication selection data;
scanning, by a scanner embedded onto a second user interface device, a machine-readable representation on the medication container to obtain recommended delivery data for the delivery of the medication, the recommended delivery data being displayed on a graphical user interface of the second user interface device, the first user interface device being separate and remote from the second user interface device;
receiving, at the second user interface device and based on the recommended delivery data, actual delivery data for the delivery of the medication; and
delivering, by a delivery device actuated by a controller receiving the actual delivery data from the second user interface device, the medication to the patient based on the actual delivery data via at least one non-infusion channel while simultaneously infusing a liquid medication to the patient, the liquid medication being different from the medication to the patient based on the actual delivery data.

24. The computer program product of claim 23, wherein the medication storage and delivery system comprises a pharmacy medication ordering system.

* * * * *